United States Patent [19]
Prüsse et al.

[11] Patent Number: 6,046,329
[45] Date of Patent: *Apr. 4, 2000

[54] URACIL DERIVATIVES

[75] Inventors: Wolfgang Prüsse, Allensbach; Wolf-Rüdiger Ulrich, Konstanz, both of Germany

[73] Assignee: Byk Gulden Lomberg Chemische Fabrik GmbH, Konstanz, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/870,436

[22] Filed: Jun. 6, 1997

Related U.S. Application Data

[63] Continuation of application No. PCT/EP95/04802, Dec. 7, 1995.

[30] Foreign Application Priority Data

Dec. 7, 1994 [CH] Switzerland ............... 3709/94

[51] Int. Cl.$^7$ ............ C07D 403/12; C07D 417/12; A61K 31/505
[52] U.S. Cl. ............ 544/295; 544/8; 514/222.5; 514/252; 514/254
[58] Field of Search ............ 544/295, 313; 514/252, 254

[56] References Cited

U.S. PATENT DOCUMENTS

| | | | |
|---|---|---|---|
| 3,235,363 | 2/1966 | Luckenbaugh et al. | 544/313 |
| 3,957,786 | 5/1976 | Klemm et al. | 260/256.4 |
| 5,332,739 | 7/1994 | Katakami et al. | 514/252 |

FOREIGN PATENT DOCUMENTS 369627  5/1990  European Pat. Off. .

OTHER PUBLICATIONS

Saxena, "Serotonin Receptors: Subtypes, Functional Responses and Therapeutic Relevance," Pharmac. Ther. vol. 66, pp. 339–368, 1995.

Hoffman, "Adrenoceptor–Blocking Drugs," Basic & Clinical Pharmacology, 6th edition, Chapter 10, pp. 132–141, 1995.

Zech et al., "Determination of Urapidil and Its Metabolites in Human Serum and Urine: Comparison of Liquid–Liquid and Fully Automated Liquid–Solid Extraction," Journal of Chromatography, 353, pp. 351–360, 1986.

Zech et al., "Biotransformation of Urapidil: Metabolites in Serum and Urine and their Biological Activity in vitro and in vivo," Arch. Internationales de Pharmacodynamie et de Therapie, 272, No. 1, pp. 180–196, 1984.

Caine, "Alpha–Adrenergic Mechanisms in Dynamics of Benign Prostatic Hypertrophy," Supplement to Urology, vol. 32, No. 6, pp. 16–20, 1988.

*Primary Examiner*—Mukund J. Shah
*Assistant Examiner*—Ann M. Kessinger
*Attorney, Agent, or Firm*—Jacobson, Price, Holman & Stern, PLLC

[57] ABSTRACT

Compounds of formula I, in which the substituents and symbols have the meanings indicated in the description, R5-$HT_{1A}$-agonists and $\alpha_1$-adrenoceptor blockers. Compositions containing these compounds as active ingredients are useful for treating those diseases which can be treated by 5-$HT_{1A}$ agonists or by $\alpha_1$-adrenoreceptor blockers.

9 Claims, No Drawings

URACIL DERIVATIVES

This application is a continuation of PCT/EP95/04802 filed Dec. 7, 1995.

FIELD OF APPLICATION OF THE INVENTION

The invention relates to compounds which are intended to be used in the pharmaceutical industry as active compounds for the production of medicaments.

KNOWN TECHNICAL BACKGROUND

U.S. Pat. No. 3,957,786 describes substituted uracil derivatives which are distinguished in particular by a marked hypotensive action.

DESCRIPTION OF THE INVENTION

Surprisingly, it has now been found that the compounds described in greater detail in the following have marked affinity for $5\text{-HT}_{1A}$ receptors and a discriminating affinity for subtypes of the $\alpha_1$ adrenoceptors.

The invention relates to compounds of formula I (see attached formula sheet), in which R1 is 1–4C-alkyl, R2 is 1–4C-alkyl, R3 is hydrogen (H), 1–7C-alkyl, 3–7C-alkenyl, 1–4C-alkoxy, halogen, halo-1–4C-alkyl, cyano-1–4C-alkyl, 1–4C-alkoxycarbonyl, nitro, hydroxyiminomethyl, methoxyiminomethyl or a group —CH$_2$—RI, in which RI is the radical bonded to the substituent R3 in formula I, A is a straight-chain or branched 1–5C-alkylene radical, Ar is a phenyl radical substituted by R4, R5 and R6, in which R4 is hydrogen, halogen, nitro, trifluoromethyl, hydroxyl, 1–4C-alkoxy, completely or partly fluorine-substituted 1–4C-alkoxy, amino or 1–4C-alkylcarbonylamino, R5 is hydrogen, halogen or 1–4C-alkoxy and R6 is hydrogen or 1–4C-alkoxy, or in which R4 and R5 are ortho to one another and together are a 1-hydroxymethylethylenedioxy radical [—O—CH(CH$_2$OH)—CH$_2$—O—] and R6 is hydrogen, X is the group NH or CO—NH, Y is oxygen (O) or sulfur (S) and Z is CO or SO$_2$, and their salts, where R3 is not hydrogen (H), 1–7C-alkyl, halogen or nitro if R4 is hydrogen, halogen, 1–4C-alkoxy or trifluoromethyl, R5 is hydrogen, halogen or 1–4C-alkoxy, R6 is hydrogen or 1–4C-alkoxy, X is the group NH, Y is oxygen (O) and Z is CO.

1–4C-Alkyl is straight-chain or branched alkyl radicals having 1 to 4 carbon atoms. Examples which may be mentioned are the butyl, isobutyl, sec-butyl, tert-butyl, propyl, isopropyl, ethyl and the methyl radical.

1–7C-Alkyl is straight-chain or branched alkyl radicals having 1 to 7 carbon atoms. Examples which may be mentioned are the heptyl, isoheptyl (2-methylhexyl), hexyl, isohexyl (2-methylpentyl), neohexyl (2,2-dimethylbutyl), pentyl, isopentyl (3-methylbutyl), neopentyl, (2,2-dimethylpropyl), butyl, isobutyl, sec-butyl, tert-butyl, propyl, isopropyl, ethyl and the methyl radical.

3–7C-Alkenyl is a straight-chain or branched alkenyl radical having 3 to 7 carbon atoms. Preferred 3–7C alkenyl radicals which may be mentioned are the 2-butenyl, the 3-butenyl, the 1-propenyl and the 2-propenyl radical (allyl radical).

1–4C-Alkoxy is a radical which, besides the oxygen atom, contains one of the abovementioned 1–4C-alkyl radicals. Examples which may be mentioned are the methoxy and the ethoxy radical.

Halogen within the meaning of the present invention is bromine, chlorine or fluorine.

Halo-1–4C-alkyl is one of the abovementioned 1–4C-alkyl radicals, which is substituted by one of the abovementioned halogen atoms. An example which may be mentioned is the 3-chloropropyl radical.

Cyano-1–4C-alkyl is one of the abovementioned 1–4C-alkyl radicals which is substituted by a cyano group. An example which may be mentioned is the 2-cyanoethyl radical.

1–4C-Alkoxycarbonyl is a radical which, besides the carbonyl group, contains one of the abovementioned 1–4C-alkoxy radicals. Examples which may be mentioned are the methoxycarbonyl and the ethoxycarbonyl radical.

Hydroxyiminomethyl is the radical —CH=N—OH, methoxyiminomethyl is the radical —CH—N—OCH$_3$.

If R3 has the meaning —CH$_2$—RI, a compound of the formula RI—CH$_2$—RI is present in which RI is the radical bonded to the substituent R3 in the formula I.

Straight-chain or branched 1–5C-alkylene is, for example, methylene (—CH$_2$), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 1,1-dimethyl-propylene [—C(CH$_3$)$_2$—CH$_2$—CH$_2$—], 2,2-dimethylethylene [—CH$_2$—C(CH$_3$)$_2$—], isopropylidene [—C(CH$_3$)$_2$—] and 1-methylethylene [—CH(CH$_3$)—CH$_2$—]. The group trimethylene (propylene) is preferred.

Examples of completely or partly fluorine-substituted 1–4C-alkoxy which may mentioned are the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radical.

1–4C-Alkylcarbonyl is a radical which, besides the carbonyl group, contains one of the abovementioned 1–4C-alkyl radicals. An example which may be mentioned is the acetyl radical.

1–4C-Alkylcarbonylamino is an amino group which is substituted by one of the abovementioned 1–4C-alkylcarbonyl radicals. An example which may be mentioned is the acetamido radical.

If R4 and R5 together are a 1-hydroxymethylethylenedioxy radical, then—together with the phenyl radical to which R4 and R5 are bonded—a 2,3-dihydro-2-hydroxymethyl-1,4-benzodioxanyl radical is present, the substituents R4 and R5 preferably being located in the 2- and 3-position relative to the phenyl bonding site, such that a 2,3-dihydro-2-hydroxymethyl-1,4-benzodioxan-5-yl radical is preferably present. This radical is a chiral radical. The invention comprises both the enantiomers and mixtures of the enantiomers in any desired mixing ratio, including the racemates. The 2,3-dihydro-2-hydroxymethyl-1,4-benzodioxan-5-yl radical is preferred in which, in the chiral carbon atom, the substituents (according to Cahn, Ingold and Prelog) are arranged in the S configuration.

Possible salts of compounds of the formula I are especially all acid addition salts. Particular mention may be made of the pharmacologically tolerable salts of the inorganic or organic acids customarily used in pharmacy. Pharmacologically untolerable salts, which, for example, can initially be obtained as process products in the preparation of the compounds according to the invention on an industrial scale, are converted into pharmacologically tolerable salts by the process known to the person skilled in the art. Those suitable as such are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether a mono- or polybasic acid is concerned, and depending on which salt is desired—in an equimolar quantitative ratio or one differing therefrom.

Particularly worthy of mention are those compounds of the formula I in which

R1 is 1–4C-alkyl,

R2 is 1–4C-alkyl,

R3 is hydrogen (H), 1–4C-alkyl, 3–4C-alkenyl, 1–4C-alkoxy, cyano-1–4C-alkyl, 1–4C-alkoxycarbonyl, hydroxyiminomethyl, methoxyiminomethyl or a group —CH$_2$—RI, in which RI is the radical bonded to the substituent R3 in formula I, A is a straight-chain 2–4C-alkylene radical, Ar is a phenyl radical substituted by R4, R5 and R6, in which R4 is hydrogen, halogen, nitro, hydroxyl, 1–4C-alkoxy, completely or partly fluorine-substituted 1–4C-alkoxy, amino or 1–4C-alkylcarbonylamino, R5 is hydrogen, halogen or 1–4C-alkoxy and R6 is hydrogen or 1–4C-alkoxy, or in which R4 and R5 are ortho to one another and together are a 1-hydroxymethylethylenedioxy radical [—O—CH(CH$_2$OH)—CH$_2$—O—] and R6 is hydrogen, X is the group NH or CO—NH, Y is oxygen (O) or sulfur (S) and Z is CO or SO$_2$, and their salts, where
R3 is not hydrogen (H) or 1–4C-alkyl, if
R4 is hydrogen, halogen or 1–4C-alkoxy,
R5 is hydrogen, halogen or 1–4C-alkoxy,
R6 is hydrogen or 1–4C-alkoxy,
X is the group NH,
Y is oxygen (O) and
Z is CO.

Furthermore particularly worthy of mention are those compounds of the formula I in which R1 is 1–4C-alkyl, R2 is 1–4C-alkyl, R3 is hydrogen (H), 1–4C-alkyl, 3–4C-alkenyl, 1–4C-alkoxy, cyano-1–4C-alkyl, 1–4C-alkoxycarbonyl, hydroxyiminomethyl, methoxyiminomethyl or a group —CH$_2$—RI, in which RI is the radical bonded to the substituent R3 in the formula I, A is a trimethylene radical, Ar is a phenyl radical substituted by R4, R5 and R6, in which R4 is hydrogen, halogen, nitro, hydroxyl, 1–4C-alkoxy, or completely or partly fluorine-substituted 1–4C-alkoxy, R5 is hydrogen, halogen or 1–4C-alkoxy and R6 is hydrogen or 1–4C-alkoxy, or in which R4 and R5 are ortho to one another and together are a 1-hydroxymethylethylenedioxy radical [—O—CH(CH$_2$OH)—CH$_2$—O—] and R6 is hydrogen, X is the group NH or CO—NH, Y is oxygen (O) and Z is CO, and their salts, where
R3 is not hydrogen (H) or 1–4C-alkyl, if
R4 is hydrogen, halogen or 1–4C-alkoxy,
R5 is hydrogen, halogen or 1–4C-alkoxy,
R6 is hydrogen or 1–4C-alkoxy, and
X is the group NH.

The invention furthermore relates to a process for the preparation of compounds of formula 1, which comprises a) reacting compounds of formula II (see attached formula sheet) in which R1, R2, R3, Y and Z have the meanings indicated above and M is a leaving group (e.g. —Br or —Cl) or a leaving group bonded to a carbonyl group (e.g. —CO—Br or —CO—Cl) with compounds of formula III (see attached formula sheet) in which A and Ar have the meanings indicated above, or b) reacting compounds of formula IV (see attached formula sheet) in which R1, R2, R3, A, X, Y and Z have the meanings indicated above and L is a leaving group (e.g. a halogen atom) with compounds of formula V (see attached formula sheet) in which Ar has the meaning indicated above, or c) reacting compounds of formula I in which R3 is hydrogen with those reactive compounds which—with removal of this hydrogen atom in a condensation reaction, or with addition of this hydrogen atom to a double bond—afford the desired substituent R3, which is other than hydrogen, or d) for the preparation of compounds I in which R3 is the group —CH$_2$—RI, reacting compounds of formula I in which R3 is hydrogen with formaldehyde, or e) for the preparation of compounds I in which R3 is hydroxyiminomethyl, reacting compounds of formula I in which R3 is —CH=O with hydroxylamine, or f) for the preparation of compounds I in which R3 is methoxyiminomethyl, methylating compounds of the formula I in which R3 is hydroxyiminomethyl, or g) for the preparation of the compounds I in which Y is sulfur (S), sulfidizing compounds of formula I in which Y is oxygen (O), or h) for the preparation of compounds I in which R4 is amino, reducing compounds of the formula I in which R4 is nitro, or I) for the preparation of compounds I in which R4 is 1–4C-alkylcarbonylamino, acylating compounds of formula I in which R4 is amino, and, if desired, then converting compounds of formula I obtained into their salts, or converting salts obtained into the free compounds.

The process corresponding to variants a) to i) is carried out as an analogous process in a manner known per se to the person skilled in the art.

The reaction is in each case carried out in suitable, inert solvents, in the presence of auxiliary reagents which may be necessary (such as, for example, auxiliary bases, for example in the variants a, b or i) and at the expedient temperature for the particular reaction.

The person skilled in the art is familiar on the basis of his expert knowledge with the solvents and auxiliary reagents which are specifically suitable, the temperatures at which to work and the reaction times which must be adhered to. The following examples serve here as an exemplary illustration.

EXAMPLES 1. 1,3,5-Trimethyl-6-[[3-[4-(3,4-dibromo-6-methoxy-phenyl)-1-piperazinyl]propyl]amino]-2,4(1H,3H)-pyrimidinedione 3.8 g (20 mmol) of 1,3,5-trimethyl-6-chloro-2,4(1H,3H)-pyrimidinedione are heated at 140° C. for 5 h with 9.6 g (20 mmol) of 1-(3-aminopropyl)-4-(3,4-dibromo-6-methoxyphenyl)piperazine and 15.2 ml (80 mmol, 11.5 ml) of tripropylamine in 40 ml of dimethyl sulfoxide.

After taking up with 600 ml of ethyl acetate, washing with 200 ml of 1N NaOH, twice with 400 ml of water and 200 ml of NaCl-saturated water, the organic phase is dried using $MgSO_4$ and evaporated. The residue is purified by column chromatography on 400 g of silica gel (eluent first ethyl acetate, later ethyl-acetate/methanol=10:1). In this manner 3.0 g (27%) of the title compound of m.p. 153–155° C. are obtained.

The precursor 1-(3-aminopropyl)-4-(3,4-dibromo-6-methoxyphenyl)piperazine is obtainable by bromination of 1-(2-methoxyphenyl)piperazine with bromine in a) conc. $H_2SO_4$ and then b) in glacial acetic acid, reaction with N-(3-bromopropyl)phthalimide to give 1-[3-(N-phthalimidopropyl)]-4-(3,4-dibromo-6-methoxyphenyl) piperazine (m.p. 158–161° C.) and cleavage with hydrazine hydrate (decomposition temperature of the dioxalate 204° C.).

2. Bis[1,3-dimethyl-6-[[3-[4-(2-methoxyhenyl)-1-piperazinyl]propyl]amino-2,4(1H,3H)-pyrimidinedione-5,5'-yl]methane 7.75 g (20 mmol) of 1,3-dimethyl-6-[[3-[4-(2-methoxyphenyl)-1-piperazinyl]propyl]amino]-2,4(1H,3H) pyrimidine-dione are treated with 50 ml of an ethanol/water mixture (80:20) and 6.4 ml (80 mmol) of a 36.3% strength aqueous formaldehyde solution and the mixture is stirred at 50° C. for 5 h. After addition of 0.4 g of KOH, it is stirred at 50° C. for a further 2 h, the solution is concentrated in vacuo to a viscous-oily residue and extracted with 50 ml of water and 100 ml of dichloromethane, the organic phase is washed with NaCl solution, dried over $Na_2SO_4$ and concentrated, and the residue is recrystallized from ethyl acetate. In this manner 6.6 g (83%) of the title compound of m.p. 133–136° C. are obtained.

The preparation of the 1,3-dimethyl-6-[3-[4-(2-methoxyphenyl)-1-piperazinyl]propyl]amino]-2,4(1H,3H)-pyrimidinedione used as a starting material is described in DE Patent Specification 1 942 405.

3. 5-Cyanoethyl-1,3-dimethyl-6-[[3-[4-(2-ethoxyphenyl)-1-piperazinyl]propyl]amino]-2,4(1H,3H)-pyrimidinedione 4.3 g (15 mmol) of 6-(3-chloropropylamino)-5-cyanoethyl-1,3-dimethyl-2,4(1H,3H)-pyrimidinedione and 4.2 g (15 mmol) of 1-(2-ethoxyphenyl)piperazine are heated at 140° C. for 14 h with 11.4 ml (60 mmol) of tripropylamine in 50 ml of xylene. The reaction mixture is concentrated in vacuo, the residue is taken up with 50 ml of water and 200 ml of ethyl acetate, and the mixture is treated with 300 ml of 1N NaOH, extracted and separated. The organic extract is washed with saturated NaCl solution and dried and the oil obtained after removing the solvent is purified by column chromatography (neutral silica gel, eluent initially ethyl acetate/petroleum ether 1:1, later only petroleum ether). The title compound of m.p. 133–136° C. (from ether) is obtained from the product fractions in a yield of 57%.

The precursor 6-(3-chloropropylamino)-5-cyanoethyl-1, 3-dimethyl-2,4(1H,3H)-pyrimidinedione is obtained by reaction of 6-(3-chloropropylamino)-1,3-dimethyl-2,4(1H, 3H)-pyrimidinedione with acrylonitrile (acetone/$K_2CO_3$, 18 h 60° C., yield 50%, m.p. 122–124° C.).

4. Bis[1,3-dimethyl-6-[[3-[4-(2-ethoxy-4-fluorophenyl)-1-piperazinyl]propyl]amino]-2,4(1H,3H)-pyrimidinedione-5,5'-yl]methane Analogously to Example 2, after stirring at RT for 20 h, the title compound of m.p. 141–143° C. (from ethyl acetate) is obtained from 1,3-dimethyl-6-[[3-[4-(2-ethoxy-4-fluorophenyl)-1-piperazinyl]propyl]amino]-2,4(1H,3H)-pyrimidinedione with formaldehyde and KOH (molar ratio 1:5:1) in a yield of 76%.

The 1,3-dimethyl-6-[3-[4-(2-ethoxy-4-fluorophenyl)-1-piperazinyl]propyl]amino]-2,4(1H,3H)-pyrimidinedione employed as starting material is prepared analogously to the starting material mentioned in Example 2 (yield 56%, m.p. 148–150° C.).

5. 1,3-Dimethyl-2,4(1H,3H)-pyrimidinedione-6-carboxylic acid [[3-[4-(2-methoxyphenyl)-1-piperazinyl]propyl] amide]

3,5 g (20 mmol) of 1,3-dimethyl-2,4(1H,3H)-pyrimidinedione-6-carboxylic acid are refluxed for 1 h with 20 ml of thionyl chloride to prepare the acid chloride. The excess thionyl chloride is distilled off in vacuo. The residue is dissolved in 10 ml of dichloromethane and 5 g (20 mmol) of 1-(2-methoxyphenyl)-4-(3-aminopropyl)piperazine and 3 g (30 mmol of triethylamine in 20 ml of dichloromethane are added dropwise with ice-cooling. After 18 h at RT 150 ml of water, 20 ml of 2N NaOH and 50 ml of dichloromethane are added, the organic phase is separated off, washed with water and dried, and the solvent is removed in vacuo. 3.6 g (43%) of the title compound of m.p. 96–99° C. are obtained from the residue (after reprecipitation from water/ethanol=4:1 and recrystallization from toluene/ether; the substance contains 0.5 mol of water).

The preparation of 1,3-dimethyl-2,4(1H,3H)-pyrimidinedione-6-carboxylic acid is described by M. P. Groziak in J. Am. Chem. Soc. 104, 6434 (1982).

6. 1,3,5-Trimethyl-6-[[3-[4-(2-tetrafluoro-ethoxyphenyl)-1-piperazinyl]-propyl]amino]-2,4(1H,3H)-pyrimidinedione Analogously to Example 1, the title compound of m.p. 120–124° C. is obtained in a yield of 15% by use of 6-chloro-1,3,5-trimethyl-2,4-(1H,3H)-pyrimidinedione and 1-(3-aminopropyl)-4-(2-tetrafluoroethoxyphenyl)piperazine with triethylamine in 20 ml of ethylene glycol monomethyl ether (16 h reflux).

The precursor 1-(3-aminopropyl)-4-(2-tetrafluoroethoxyphenyl)piperazine is obtained analogously to the precursor described in Example 1 by cleavage of 1-(N-phthalimidopropyl)-4-(2-tetrafluoroethoxyphenyl)-piperazine according to a known method (yield 35%, decomposition temperature of the dihydrochloride, which contains 1 mol of water, 153° C.).

7. 5-Allyl-1,3-dimethyl-6-[[3-[4-(2-ethoxy-4-fluorophenyl)-1-piperazinyl]propyl]amino]-2,4(1H,3H)-pyrimidinedione Analogously to Example 3, the title compound of m.p. 103–105° C. is obtained in a yield of 55% by reaction of 5-allyl-1,3-dimethyl-6-(3-chloropropylamino)-2,4(1H,3H)-pyrimidinedione with 1-(2-ethoxy-4-fluorophenyl)-piperazine in xylene and tripropylamine (14 h reflux) after purification by column chromatography.

The starting material 5-allyl-1,3-dimethyl-6-(3-chloropropylamino)-2,4(1H,3H)-pyrimidinedione is obtained by reaction of 1,3-dimethyl-6-(3-chloropropylamino)-2,4(1H,3H)-pyrimidinedione with allyl bromide (acetone/$K_2CO_3$, 70 h 60° C.), yield 80%, m.p. 74–76° C.

The hydrochloride of 1-(2-ethoxy-4-fluorophenyl)-piperazine is obtained from 2-ethoxy-4-fluoroaniline and bis(2-chloroethyl)amine; yield 56%, m.p. 199–200° C.

8. 5-Cyanoethyl-1,3-dimethyl-6-[[3-[4-(2-tetrafluoroethoxyphenyl)-1-piperazinyl-propyl]amino]-2,4(1H,3H)-pyrimidinedione Analogously to Example 3, the title compound is obtained from 5-cyanoethyl-6-(3-chloropropylamino)-1,3-dimethyl-2,4(1H,3H)-pyrimidinedione with 1-(2-tetrafluoroethoxyphenyl)piperazine. Yield 41%, m.p. 130–132° C.

The 1-(2-tetrafluoroethoxyphenyl)piperazine used as starting material is obtained from 2-tetrafluoroethoxyaniline and bis(2-chloroethyl)amine (yield of oily hydrochloride 44%).

9. 1,3,5-Trimethyl-6-[[3-[4-((2,3-dihydro-2-hydroxymethyl)-1,4-benzodioxin-5-yl)-1-piperazinyl]propyl]amino]-2,4(1H,3H)-pyrimidinedione Analogously to Example 1, the title compound (yield 61% m.p. 119–122° C.) is prepared using 1-(3-aminopropyl)-4-((2,3-dihydro-2-hydroxymethyl)-1,4-benzodioxin-5-yl)-piperazine, which is obtained by cleavage of the corresponding phthalimido compound (yield 73%, oil).

1-(3-Aminopropyl)-4-((2,3-dihydro-2-hydroxymethyl)-1,4-benzodioxin-5-yl)piperazine, is obtainable from 1-((2,3-dihydro-2-hydroxymethyl)-1,4-benzodioxin-5-yl)-piperazine (whose benzoic acid ester is described in EP 138280) analogously to the preparation of the precursor of Example 1 with N-(3-bromopropyl)phthalimide and cleavage with hydrazine hydrate (yield 73%).

10. Bis[1,3-dimethyl-6-[[3-[4-((2,3-dihydro-2-hydroxymethyl)-1,4-benzodioxin-5-yl)-1-piperazinyl]propyl]amino]-2,4(1H,3H)-pyrimidinedione-5,5'-yl]methane Analogously to Example 2 or 4, the title compound is obtained in a yield of 83% with an m.p. of 134–137° C. by use of 1,3-dimethyl-6-[[3-[4-((2,3-dihydro-2-hydroxymethyl)-1,4-benzodioxin-5-yl)-1-piperazinyl]-propyl]-amino]-2,4(1H,3H)-pyrimidinedione.

The starting compound can be obtained by reaction of 6-(3-chloropropylamino)-1,3-dimethyl-2,4(1H,3H)-pyrimidinedione with 1-((2,3-dihydro-2-hydroxymethyl)-1,4-benzodioxin-5-yl)piperazine (yield 55%, decomposition temperature of the trihydrochloride 208° C.).

11. 5-Allyl-1,3-dimethyl-6-[[3-[4-(2-tetrafluoroethoxyphenyl)-1-piperazinyl]propyl]amino]-2,4(1H,3H)-pyrimidinedione The pyrimidinedione of Example 7 and the piperazine of Example 8 are reacted according to the method of Example 3. The title compound is obtained in a yield of 25% with a decomposition temperature of the fumarate of 145° C.

12. 1,3-Dimethyl-5-ethoxycarbonyl-6-[[3-[4-(2-methoxyhenyl)-1-piperazinyl]propyl]amino]-2,4(1H,3H)-pyrimidinedione The reaction of the starting compound of Example 2 with ethyl chloroacetate (suspension in pyridine, initially 0° C., then 1 h at 22° C., then 0.5 h reflux, purification by column chromatography) affords the title compound of m.p. 104–106° C. in 39% yield.

13. 1,3,5-Trimethyl-6-[[3-[4-(2-hydroxyphenyl)-1-piperazinyl]propyl]amino]-2,4(1H,3H)-pyrimidinedione The 1,3,5-trimethyl-6-(3-chloropropylamino)-2,4(1H,3H)-pyrimidinedione prepared from 6.8 g (30 mmol) of 1,3,5-trimethyl-6-(3-hydroxypropylamino)-2,4(1H,3H) pyrimidinedione with thionyl chloride is refluxed for 15 h with 4.5 g (25 mmol) of 1-(2-hydroxyphenyl)piperazine in 140 ml of xylene and 20 ml of tripropylamine. The dark oil obtained after customary work-up is purified by column chromatography on silica gel using dichloromethane/methanol (1–10%). From the product fractions, the fumarate is precipitated from ethyl acetate/ethanol using fumaric acid, yield 5.9 g (47%), m.p. 203–205° C.

The starting compound 1-(2-hydroxyphenyl)piperazine of m.p. 125–128° C. is obtained in a yield of 92% by cleavage of 1-(2-methoxyphenyl)piperazine with pyridine hydrochloride according to a known process (molar ratio 1:10, 4 h 180° C.).

14. 1,3,5-Trimethyl-6-[[3-[4-(2-methoxy-4-nitrophenyl)-1-piperazinyl]propyl]amino]-2,4(1H,3H)-pyrimidinedione Analogously to Example 13, 1,3,5-trimethyl-6-(3-chloropropylamino)-2,4(1H,3H)-pyrimidinedione (130 mmol) is refluxed for 14 h with 1-(2-methoxy-4-nitrophenyl)piperazine (100 mmol) and tripropylamine (75 ml) in 300 ml of diglyme. After removing the solvent in vacuo, the mixture is worked up in the customary manner, and after purification by column chromatography, the title compound is obtained in 79% yield (m.p. 131–133° C.).

1-(2-Methoxy-4-nitrophenyl)piperazine is obtained after nitration of 1-acetyl-4-(2-methoxyphenyl)piperazine with 33% strength nitric acid in glacial acetic acid and subsequent hydrolysis by boiling with conc. hydrochloric acid, yield 58%, m.p. 89–91° C.

15. 1,3-Dimethyl-5-methoxyiminomethyl-6-[[3-[4-(2-methoxyohenyl)-1-piperazinyl]propyl]amino]-2,4(1H,3H)-pyrimidinedione 20.1 g (43,5 mmol) of 1,3-dimethyl-5-hydroxyiminomethyl-6-[[3-[4-(2-methoxyphenyl)-1-piperazinyl]propyl]amino]-2,4(1H,3H)-pyrimidinedione are dissolved in 100 ml of ethanol, 11.6 ml (61 mmol) of 30% strength sodium methoxide solution and 5.8 ml (7.7 g, 61 mmol) of dimethyl sulfate are added and the mixture is refluxed for 2 h. After distilling off the ethanol in vacuo, the residue is treated with 100 ml of water and 50 ml of 1N NaOH and extracted three times with 75 ml of dichloromethane; the combined extracts are dried over magnesium sulfate and the evaporation residue is recrystallized from 50 ml of ethanol. 14.6 g (76%) of the title compound with an m.p. of 107–109° C. are obtained in this manner.

16. 1,3-Dimethyl-5-hydroxyiminomethyl-6-[[3-[4-(2-methoxphenyl)-1-piperazinyl]propyl]amino]-2,4(1H,3H)-pyrimidinedione The title compound is obtained using hydroxylamine hydrochloride/sodium acetate in ethanol (2 h reflux) from 1,3-dimethyl-5-formyl-6-[[3-[4-(2-methoxyphenyl)-1-piperazinyl]propyl]amino]-2,4(1H,3H)-pyrimidinedione, which is obtained from 1,3-dimethyl-6-[[3-[4-(2-methoxyphenyl)-1-piperazinyl]propyl]amino]-2,4(1H, 3H)-pyrimidinedione by reaction with $POCl_3$/DMF according to Vilsmeier-Haack (yield 78%, m.p. 121–123° C.). Yield after recrystallization from methanol 48% of the methanol adduct, decomposition temperature from 96° C.

17. 1,3-Dimethyl-5-methoxy-6-[3-(4-[2-methoxyphenyl]-1-piperazinyl)propyl]amino]-2,4-(1H,3H)-pyrimidinedione In a manner analogous to that described in Example 1, the title compound of m.p. 112–113° C. is obtained in 79% yield from 1,3-dimethyl-5-methoxy-6-chloro-2,4(1H,3H)-pyrimidinedione and 1-(3-aminopropyl)-4-(2-methoxyphenyl)piperazine.

18. 5-{3-[4-(2-Methoxyphenyl)piperazin-1-yl]-propylamino}-2,6-dimethyl-1,1-dioxo-6H-[1,2,6]thiadiazin-3-one Analogously to Example 1, the title compound of m.p. 137–139° C. is obtained using 120 mmol of 6H-2,3-dihydro-2,6-dimethyl-3-oxo-5-chloro-1,2,6-thiadiazine-1,1-dioxide and 240 mmol of 1-(2-methoxyphenyl)-4-(3-aminopropyl) piperazine by fusing at 125° C. for 1.5 hours and after purification by means of column chromatography on silica gel and recrystallization from ethyl acetate (yield 36%).

The starting compound 6H-2,3-dihydro-2,6-dimethyl-3-oxo-5-chloro-1,2,6-thiadiazine-1,1-dioxide is obtainable by chlorination of the 5-hydroxy compound with $POCl_3/H_3PO_4$ (2 h reflux), yield 40%, m.p. 51–2° C. The preparation of the hydroxy compound is known and is carried out by reaction of dimethylsulfamide and malonyl dichloride [P. Goya et al., Can. J. Chem. 65, 298 (1987)], yield 89%, m.p. 92–93° C.

19. 6-{3-[4-(2-Methoxyphenyl)piperazin-1-yl]-propylamino}-1,3-dimethyl-4-thioxo-3,4-dihydro-1H-pyrimidin-2-one.

According to the method of A. R. Lapucha, Synthesis 1987, 256, 35% of the title compound of m.p. 171–174° C. is obtained from 10 mmol each of 1,3-dimethyl-6-[(3-[(2-methoxyphenyl)-1-piperazinyl]propyl)amino]-2,4(1H,3H)-pyrimidinedione and tetraphosphorus decasulfide $P_4S_{10}$ in 15 ml of diglyme and 40 mmol of $NaHCO_3$ (heating at 140° C. for 4 h).

20. 1,3,5-Trimethyl-6-[[3-[4-(4-amino-2-methoxyphenyl)-1-piperazinyl]propyl]amino]-2,4(1H,3H)-pyrimidinedione 50 mmol of 1,3,5-trimethyl-6-[(3-[4-(2-methoxy-4-nitrophenyl)-1-piperazinyl]propyl)amino]-2,4(1H,3H)-pyrimidinedione are reduced using hydrazine hydrate/Raney-Nickel in ethanol/water according to a known method. After purification by column chromatography and recrystallization from ethyl acetate, 73% of the title compound of m.p. 146–148° C. is obtained. The starting substance is the product of Example 14.

21. 1,3,5-Trimethyl-6-[[3-[4-(4-acetylamino-2-methoxyphenyl)-1-piperazinyl]propyl]amino]-2,4(1H,3H)pyrimidinedione The substance of Example 20 is acetylated in a known manner using acetic anhydride (1 h 110° C.). The title compound of m.p. 178–180° C. is obtained in a yield of 28%.

Commercial Utility

The compounds of the formula I and their salts have useful pharmacological properties which make them commercially utilizable. In particular, they have a high affinity for 5-$HT_{1A}$ receptor binding sites. Moreover, they are distinguished by a discriminating $\alpha_1$ adrenoceptor subtype-antagonistic activity. In spite of their affinity for the 5-$HT_{1A}$ binding site and for $\alpha_1$ receptor subtypes, however, they have only a comparatively less strongly marked hypotensive action.

In their excellent properties, which are associated with a great therapeutic breadth and the absence of significant side effects, the compounds according to the invention and their salts prove to be particularly suitable for use in human and veterinary medicine, where they can be employed in particular for the treatment of those diseases which can be treated by 5-$HT_{1A}$ agonists or $\alpha_1$ adrenoreceptor blockers. In this connection, illnesses are especially to be mentioned which are based on central nervous disorders (e.g. acute and chronic anxiety states, depression, anorexia, sexual disorders, psychoses), sleep disorders, senile disorders of the mental function (e.g. senile dementia), cerebral ischemias, cerebral apoplexy, and also illnesses which are accompanied by excess vasoconstriction (e.g. arterial high blood pressure) or increased muscle contraction in certain areas (e.g. neurogenic bladder disorders, prostate hypertrophy).

The invention therefore furthermore relates to the compounds according to the invention for use in the treatment and/or prophylaxis of the abovementioned illnesses.

The invention likewise comprises the use of the compounds according to the invention for the production of medicaments which are employed for the treatment and/or prophylaxis of the abovementioned illnesses.

The invention furthermore comprises the use of the compounds according to the invention for the treatment and/or prophylaxis of the abovementioned illnesses.

The invention furthermore relates to medicaments which contain one or more compounds of the formula I and/or their pharmacologically tolerable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form (e.g. a depot form or an enteric form) exactly suited to the active compound and/or to the desired onset of action by the appropriate choice of the auxiliaries and excipients.

The person skilled in the art is familiar on the basis of his expert knowledge with the auxiliaries and excipients which are suitable for the desired pharmaceutical formulations. Besides solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.05 to approximately 30, preferably 0.1 to 10, in particular 0.2 to 6, mg/kg of body weight, if appropriate in the form of several, preferably 1 to 4, individual doses to achieve the desired result. In the case of parenteral treatment, similar or (in particular in the case of intravenous administration of the active compounds) as a rule lower doses can be used. Any person skilled in the art can easily fix the optimum dose necessary in each case and manner of administration of the active compounds on the basis of his expert knowledge.

If the compounds and/or salts according to the invention are to be employed for the treatment of the abovementioned illnesses, the pharmaceutical preparations can also contain one or more pharmacologically active constituents of other pharmaceutical groups, such as antacids, for example aluminum hydroxide, magnesium aluminate; tranquilizers, such as benzodiazepines, for example diazepam; spasmolytics, such as, for example, bietamiverine, camylofin, anticholinergics, such as, for example, oxyphencyclimine, phencarbamide; local anesthetics, such as, for example, tetracaine, procaine; and if desired also enzymes, vitamins or amino acids.

Biological Investigations

Determination of the affinities of substances for $\alpha_1$ receptor subtypes and 5-HT$_{1A}$ receptors.

The affinity of substances for $\alpha_1$ receptor subtypes was determined in radioligand binding studies using [$^3$H] prazosine as a radioligand. 50–200 µg of membranes from rat brain cortex were incubated in a total volume of 0.5–1 ml with [$^3$H]prazosine (0.2 to 0.5 nmol/l) in the presence of rising concentrations of substances. The incubation buffer used was 50 mmol/l tris/HCl pH 7.5, 1 mmol/l EDTA, 0.1 mmol/l PMSF. The nonspecific binding was determined in separate batches in the presence of 10 µmol/l of phentolamine or 1 µmol/l of prazosine. After 1 h at 37° C., the bound radioactivity was separated from the free radioactivity by rapid filtration of the incubation batch at 0° C. through glass fiber filters. The filters were washed twice with 3.5 ml each of cold filtration buffer (50 mmol/l tris/HCl pH 7.4, 10 mmol/l MgCl$_2$, 10% polyethylene glycol 6000). The filter-bound radioactivity was determined by liquid scintillation counting. Substances with subtype selectivity for the $\alpha_1$ receptor subtypes were tested again in the presence of 3 nmol/l of WB 4101. WB4101 blocks the binding of [$^3$H] prazosine to the $\alpha_{1A}$ receptor subtype and the remaining binding corresponds to that to the $\alpha_{1B}$ receptor.

The affinity of substances for the 5-HT$_{1A}$ receptor was determined in radioligand binding studies using [$^3$H]8-OH-DPAT as a radioligand. 50–150 µg of membranes from pig brain cortex were incubated in a total volume of 0.25–0.5 ml with [$^3$H]8-OH-DPAT (0.2 to 0.4 nmol/l) in the presence of rising concentrations of substances. The incubation buffer used was 50 mmol/l tris/HCl pH 8.2, 1 mmol/l MnCl$_2$. The nonspecific binding was determined in separate batches in the presence of 10 µmol/l of 5-HT. After 30 min at 23° C., the bound radioactivity was separated from the free radioactivity by rapid filtration of the incubation batch at 0° C. through glass fiber filters. The filters were washed twice with 3.5 ml each of cold filtration buffer (50 mmol/l tris/HCl pH 7.4, 10 mmol/l MgCl$_2$, 10% polyethylene glycol 6000). The filter-bound radioactivity was determined by liquid scintillation counting.

For each substance, dose-response curves were plotted by means of nonlinear regression using the Inplot program (GraphPad, Sorento, Calif., USA). IC$_{50}$ values were corrected by the concentration of the radioligand employed according to the formula of Cheng and Prusoff. The resulting K$_I$ values (see following table) represent the affinity of the respective substance for the tested receptor. The compounds according to the invention investigated according to the model illustrated in greater detail above have been provided in the following table with numbers which correspond to the numbers of these compounds in the examples.

TABLE

Affinity of the compounds according to the invention for $\alpha_1$ receptor subtypes and 5-HT$_{1A}$ receptors, expressed in pK$_I$ values

| Compound | | Receptor affinity | | |
|---|---|---|---|---|
| B No. | No. | $\alpha_{1A}$ | $\alpha_{1B}$ | 5-HT$_{1A}$ |
| B8805-004 | 1 | 8.3 | 8.3 | 8.9 |
| B8805-005 | 2 | 9.4 | 9.4 | 7.9 |
| B8805-006 | 3 | 9.3 | 7.2 | 9.4 |
| B8805-015 | 4 | 9.0 | 9.0 | 7.4 |
| B8805-016 | 5 | 8.3 | 6.6 | 8.6 |
| B8805-029 | 6 | 9.4 | 7.5 | 9.7 |
| B8805-031 | 7 | 9.2 | 7.4 | 9.1 |
| B8805-035 | 8 | 9.2 | 7.5 | 10.0 |
| B8805-033 | 9 | 8.7 | 5.8 | 9.7 |
| B8805-032 | 10 | 8.1 | 8.1 | 9.3 |
| B8805-037 | 11 | 9.6 | 7.9 | 9.3 |
| B8905-001 | 12 | 7.6 | 7.6 | 8.2 |
| B8905-002 | 13 | 7.7 | 7.7 | 9.6 |
| B8905-006 | 14 | 6.6 | 6.6 | 6.7 |
| B8905-020 | 15 | 8.3 | 6.9 | 8.8 |
| B7705-036 | 16 | 8.7 | 7.3 | 9.0 |
| B8805-012 | 17 | 7.3 | 7.3 | 8.6 |
| B8805-022 | 18 | 8.2 | 6.9 | 7.8 |
| B8805-036 | 19 | 7.5 | 7.5 | 8.0 |
| B8905-022 | 20 | 7.0 | 5.2 | 8.7 |
| B8905-030 | 21 | <5 | <5 | 8.3 |

FORMULA SHEET

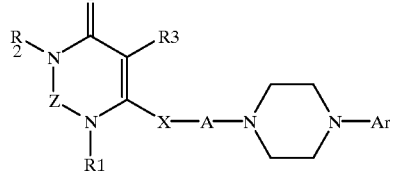

(I)

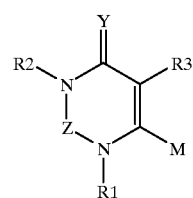

(II)

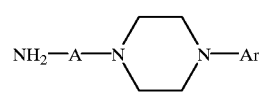

(III)

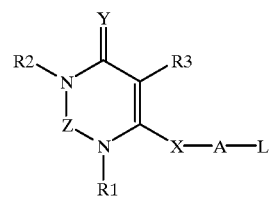

(IV)

(V)

We claim:
1. A compound of the formula I

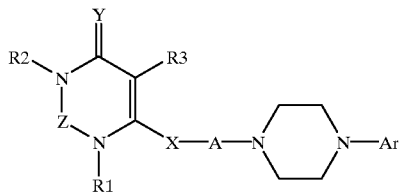

in which
R1 is 1–4C-alkyl,
R2 is 1–4C-alkyl,
R3 is hydrogen (H), 1–7C-alkyl,3–7C-alkenyl, 1–4C-alkoxy, halogen, halo-1–4C-alkyl, cyano-1–4C-alkyl, 1-4C-alkoxycarbonyl, nitro, hydroxyiminomethyl, methoxyiminomethyl or a group —CH$_2$—RI, in which RI is the radical bonded to the substituent R3 in formula I,
A is a straight-chain or branched 1–5C-alkylene radical,
Ar is a phenyl radical substituted by R4, R5 and R6, in which
R4 is hydrogen, halogen, nitro, trifluoromethyl, hydroxyl, 1–4C-alkoxy, completely or partly fluorine-substituted 1–4C-alkoxy, amino or 1–4C-alkylcarbonylamino,
R5 is hydrogen, halogen or 1–4C-alkoxy and
R6 is hydrogen or 1–4C-alkoxy, or in which
R4 and R5 are ortho to one another and together are a 1-hydroxymethylethylenedioxy radical [—O—CH(CH$_2$OH)—CH$_2$—O—] and
R6 is hydrogen,
X is the group NH or CO—NH,
Y is sulfur (S) and
Z is CO,
or a salt thereof.

2. A compound of formula I

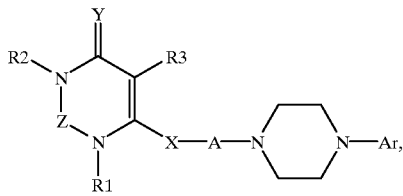

in which
R1 is 1–4-C-alkyl,
R2 is 1–4C-alkyl,
R3 is a group —CH$_2$—RI, in which RI is the radical bonded to the substituent R3 in formula I,
A is a straight-chain 2–4C-alkylene radical,
Ar is a phenyl radical substituted by R4, R5 and R6, in which
R4 is hydrogen, halogen, nitro, hydroxyl, 1–4C-alkoxy, completely or partly fluorine-substituted 1–4C-alkoxy, amino or 1–4C-alkylcarbonylamino,
R5 is hydrogen, halogen or 1–4C-alkoxy and
R6 is hydrogen or 1–4C-alkoxy, or in which
R4 and R5 are ortho to one another and together are a 1-hydroxymethylethylenedioxy radical {—O—CH(CH$_2$OH)—CH$_2$—O} and
R6 is hydrogen,
X is the group NH or CO—NH,
Y is oxygen (O) or sulfur (S) and
Z is CO,
or a salt thereof.

3. A compound of formula I

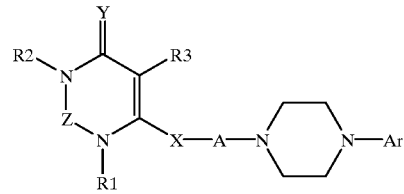

in which
R1 is 1–4C-alkyl,
R2 is 1–4C-alkyl,
R3 is hydrogen (H), 1–7C-alkyl,3–7C-alkenyl, 1–4C-alkoxy, halogen, halo-1–4C-alkyl, cyano-1–4C-alkyl, 1–4C-alkoxycarbonyl, nitro, hydroxyiminomethyl, methoxyiminomethyl or a group —CH$_2$—RI, in which RI is the radical bonded to the substituent R3 in formula I,
A is a straight-chain or branched 1–5C-alkylene radical,
Ar is a phenyl radical substituted by R4, R5 and R6, in which
R4 is hydrogen, halogen, nitro, trifluoromethyl, hydroxyl, 1–4C-alkoxy, completely or partly fluorine-substituted 1–4C-alkoxy, amino or 1–4C-aklylcarbonylamino,
R5 is hydrogen, halogen or 1–4C-alkoxy and
R6 is hydrogen or 1–4C-alkoxy, or in which
R4 and R5 are ortho to one another and together are a 1-hydroxymethylethylenedioxy radical [—O—CH(CH$_2$OH)—CH$_2$—O—] and
R6 is hydrogen,
X is CO—NH,
Y is oxygen (O) or sulfur (S) and
Z is CO,
or a salt thereof.

4. A compound of formula I

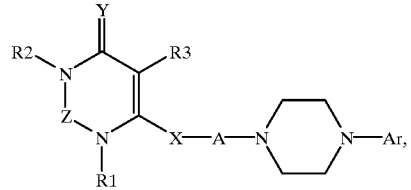

in which
R1 is 1–4-C-alkyl,
R2 is 1–4C-alkyl,
R3 is 1–4C-alkyl, 3–4C-alkenyl, 1–4C-alkoxy, cyano-1–4C-alkyl, 1-4C-alkoxycarbonyl, hydroxyiminomethyl, methoxyiminomethyl or a group —CH$_2$—RI, in which RI is the radical bonded to the substituent R3 in formula I, A is a straight-chain 2–4C-alkylene radical, Ar is a phenyl radical substituted by R4, R5 and R6, in which
- R4 and R5 are ortho to one another and together are a 1-hydroxymethylethylenedioxy radical {—O—CH(CH₂OH)—CH₂—O} and
- R6 is hydrogen, X is the group NH or CO—NH, Y is oxygen (O) or sulfur (S) and Z is CO, or a salt thereof.

5. A compound of claim 4 wherein

R1 is methyl,

R2 is methyl,

R3 is methyl,

A is trimethylene (propylene),

X is NH, and

Y is oxygen (O).

6. A compound of formula I

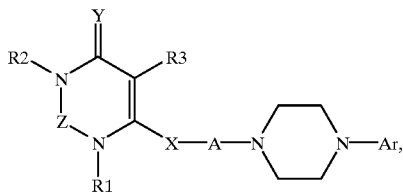

(I)

in which

R1 is 1–4-C-alkyl,

R2 is 1–4C-alkyl,

R3 is 3–4C-alkenyl,

A is a straight-chain 2–4C-alkylene radical,

Ar is a phenyl radical substituted by R4, R5 and R6, in which
- R4 is hydrogen, halogen, nitro, hydroxyl, 1–4C-alkoxy, completely or partly fluorine-substituted 1–4C-alkoxy, amino or 1–4C-alkylcarbonylamino,
- R5 is hydrogen, halogen or 1–4C-alkoxy and
- R6 is hydrogen or 1–4C-alkoxy, or in which
- R4 and R5 are ortho to one another and together are a 1-hydroxymethylethylenedioxy radical {—O—CH(CH₂OH)—CH₂—O} and
- R6 is hydrogen, X is the group NH or CO—NH, Y is oxygen (O) or sulfur (S) and Z is CO, or a salt thereof.

7. A compound of formula I

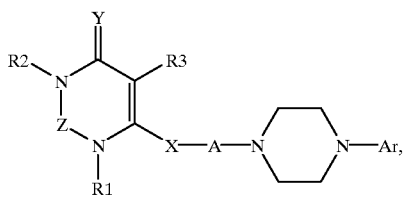

(I)

in which

R1 is 1–4-C-alkyl,

R2 is 1–4C-alkyl,

R3 is 1–4C-alkoxy,

A is a straight-chain 2–4C-alkylene radical,

Ar is a phenyl radical substituted by R4, R5 and R6, in which
- R4 is hydrogen, halogen, nitro, hydroxyl, 1–4C-alkoxy, completely or partly fluorine-substituted 1–4C-alkoxy, amino or 1–4C-alkylcarbonylamino,
- R5 is hydrogen, halogen or 1–4C-alkoxy and
- R6 is hydrogen or 1–4C-alkoxy, or in which
- R4 and R5 are ortho to one another and together are a 1-hydroxymethylethylenedioxy radical {—O—CH(CH₂OH)—CH₂—O} and
- R6 is hydrogen, X is the group NH or CO—NH, Y is oxygen (O) or sulfur (S) and Z is CO, or a salt thereof.

8. A compound of formula I

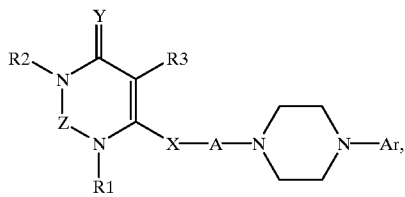

(I)

in which

R1 is 1–4-C-alkyl,

R2 is 1–4C-alkyl,

R3 is 1–4C-alkoxycarbonyl,

A is a straight-chain 2–4C-alkylene radical,

Ar is a phenyl radical substituted by R4, R5 and R6, in which
- R4 is hydrogen, halogen, nitro, hydroxyl, 1–4C-alkoxy, completely or partly fluorine-substituted 1–4C-alkoxy, amino or 1–4C-alkylcarbonylamino,
- R5 is hydrogen, halogen or 1–4C-alkoxy and
- R6 is hydrogen or 1–4C-alkoxy, or in which
- R4 and R5 are ortho to one another and together are a 1-hydroxymethylethylenedioxy radical {—O—CH(CH₂OH)—CH₂—O} and
- R6 is hydrogen, X is the group NH or CO—NH, Y is oxygen (O) or sulfur (S) and Z is CO, or a salt thereof.

9. A compound of formula I

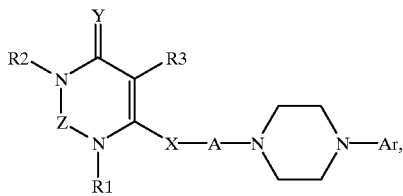
(I)

in which
R1 is 1–4-C-alkyl,
R2 is 1–4C-alkyl,
R3 is hydroxy- or methoxy-iminomethyl,
A is a straight-chain 2–4C-alkylene radical,
Ar is a phenyl radical substituted by R4, R5 and R6, in which
R4 is hydrogen, halogen, nitro, hydroxyl, 1–4C-alkoxy, completely or partly fluorine-substituted 1–4C-alkoxy, amino or 1–4C-alkylcarbonylamino,
R5 is hydrogen, halogen or 1–4C-alkoxy and
R6 is hydrogen or 1–4C-alkoxy, or in which
R4 and R5 are ortho to one another and together are a 1-hydroxymethylethylenedioxy radical {—O—CH(CH$_2$OH)—CH$_2$—O} and
R6 is hydrogen,
X is the group NH or CO—NH,
Y is oxygen (O) or sulfur (S) and
Z is CO,
or a salt thereof.

* * * * *